US008592392B2

(12) United States Patent
Prasad et al.

(10) Patent No.: US 8,592,392 B2
(45) Date of Patent: *Nov. 26, 2013

(54) MULTIPLE ANTIOXIDANT MICRONUTRIENTS

(75) Inventors: Kedar N Prasad, San Rafael, CA (US); Gerald M Haase, Greenwood Village, CO (US)

(73) Assignee: Premier Micronutrient Corporation, Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/032,831

(22) Filed: Jan. 11, 2005

(65) Prior Publication Data

US 2005/0119218 A1 Jun. 2, 2005

Related U.S. Application Data

(63) Continuation of application No. 10/229,271, filed on Aug. 28, 2002, now Pat. No. 6,849,613.

(51) Int. Cl.
*A61K 31/714* (2006.01)

(52) U.S. Cl.
USPC .............. 514/52; 514/275; 514/184; 514/458; 514/168; 514/725

(58) Field of Classification Search
USPC ............ 514/52, 188, 167, 251, 474, 494, 458
See application file for complete search history.

(56) References Cited

U.S. PATENT DOCUMENTS

| 2,939,821 | A | | 6/1960 | Eigen et al. | 514/52 |
|---|---|---|---|---|---|
| 3,446,899 | A | | 5/1969 | Louis et al. | 514/474 |
| 3,584,114 | A | | 6/1971 | Cavalli | 424/465 |
| 3,777,029 | A | | 12/1973 | Magrid | 514/356 |
| 4,619,829 | A | | 10/1986 | Motschan | 424/602 |
| 4,740,373 | A | | 4/1988 | Kesselman et al. | 424/638 |
| 4,976,960 | A | | 12/1990 | Grossman et al. | 424/750 |
| 5,084,482 | A | | 1/1992 | Hirsch et al. | 514/562 |
| 5,223,285 | A | | 6/1993 | DeMichele et al. | 426/72 |
| 5,292,538 | A | | 3/1994 | Paul et al. | 426/74 |
| 5,561,160 | A | * | 10/1996 | Walaszek et al. | 514/574 |
| 5,571,441 | A | | 11/1996 | Andon et al. | 252/1 |
| 5,626,883 | A | | 5/1997 | Paul | 424/605 |
| 5,629,023 | A | | 5/1997 | Bland | 424/655 |
| 5,788,971 | A | | 8/1998 | Togasaki | 424/729 |
| 5,895,652 | A | * | 4/1999 | Giampapa | 424/195.17 |
| 5,922,346 | A | | 7/1999 | Hersh | 424/439 |
| 5,922,704 | A | | 7/1999 | Bland | 514/185 |
| 5,939,394 | A | | 8/1999 | Fleming et al. | 514/23 |
| 5,948,823 | A | | 9/1999 | Ben-Amotz | 514/763 |
| 5,976,568 | A | | 11/1999 | Riley | 424/451 |
| 5,985,339 | A | | 11/1999 | Kamarei | 426/72 |
| 6,048,846 | A | | 4/2000 | Cochran | 514/168 |
| 6,066,327 | A | | 5/2000 | Gubernick | 424/401 |
| 6,068,848 | A | | 5/2000 | Gubernick | 424/401 |
| 6,080,788 | A | | 6/2000 | Sole et al. | 514/561 |
| 6,090,414 | A | | 7/2000 | Passwater et al. | 424/702 |
| 6,117,872 | A | | 9/2000 | Maxwell et al. | 514/249 |
| 6,124,268 | A | | 9/2000 | Ghosal | 514/27 |
| 6,130,244 | A | | 10/2000 | DeMichele et al. | 514/474 |
| 6,162,468 | A | | 12/2000 | Stanley et al. | 424/600 |
| 6,194,452 | B1 | | 2/2001 | Murad | 514/474 |
| 6,245,360 | B1 | * | 6/2001 | Markowitz | 424/641 |
| 6,254,898 | B1 | | 7/2001 | Bragaglia | 424/729 |
| 6,255,341 | B1 | | 7/2001 | DeMichele et al. | 514/474 |
| 6,258,384 | B1 | | 7/2001 | Stanley et al. | 424/600 |
| 6,291,533 | B1 | * | 9/2001 | Fleischner | 514/52 |
| 6,326,034 | B1 | | 12/2001 | Mirsky et al. | 424/725 |
| 6,329,414 | B1 | | 12/2001 | Thomas et al. | 514/400 |
| 6,362,167 | B1 | | 3/2002 | Ghosal | 514/25 |
| 6,379,664 | B1 | | 4/2002 | Lou et al. | 424/94.5 |
| 6,426,076 | B1 | | 7/2002 | Pascoe | 424/400 |
| 6,426,362 | B1 | | 7/2002 | Miller et al. | 514/458 |
| 6,444,221 | B1 | | 9/2002 | Shapiro | 424/451 |
| 6,444,700 | B1 | | 9/2002 | DeMichele et al. | 514/474 |
| 6,451,341 | B1 | * | 9/2002 | Slaga et al. | 424/468 |
| 6,503,529 | B1 | * | 1/2003 | Fleischner | 424/439 |
| 6,573,299 | B1 | | 6/2003 | Petrus | 514/558 |
| 6,579,544 | B1 | | 6/2003 | Rosenberg et al. | 424/736 |
| 6,602,512 | B1 | | 8/2003 | Cavazza | 424/400 |
| 6,632,459 | B2 | | 10/2003 | Graus et al. | 424/728 |

(Continued)

OTHER PUBLICATIONS

Simon-Schnass I (1994). Risk of oxidative stress during exercise at high altitude. In: Sen CK, Packer L, Hanninen O, eds. Exercise and oxygen toxicity. New York, NY: Elsevier Science B.V., 191-210.
Renold AE, Mintz DH, Muller WA, Cahill, Jr GF: Diabetes mellitus: In: Stanbury JB, Wyngaarden JB, and Frederickson DS, eds. The metabolic basis of inherited diseases. New York: McGraw-Hill, 80-109, 1978.
Suzuki YJ, Tsuchiya M, Packer L: Lipoate prevents glucose-induced protein modifications. Free Rad Res Commun 17:211-217, 1992.
Salonen, J. T.; Clinical trials testing cardiovascular benefits of antioxidant supplementation. Free Radic Res. 36:1299-1306; 2002.
Carter, C. A., Pogribny, M., Davidson, A., Jackson, C. D., McGarrity, L. J., Morris, S. M.; Effects of retinoic acid on cell differentiation and reversion toward normal in human endometrial adenocarcinoma (RL95-2) cells. Anticancer Res. 16:17-24; 1996.

(Continued)

*Primary Examiner* — Melenie McCormick
*Assistant Examiner* — Taina D Matos Negron
(74) *Attorney, Agent, or Firm* — Dan M. DeLaRosa

(57) ABSTRACT

A method for optimizing the health of humans according to their age and sex is disclosed wherein the method comprises administering to said humans a daily dose of a multiple antioxidant micronutrient composition comprising vitamin A (palmitate), beta-carotene (from natural d. salina), vitamin C (calcium ascorbate), vitamin D-3 (cholecalciferol), natural source vitamin E including both d-alpha tocopherol and d-alpha tocopheryl acid succinate, thiamine mononitrate, riboflavin, niacinamide ascorbate, d-calcium pantothenate, pyridoxine hydrochloride, cyanocobalamin, folic acid (folacin), d-biotin, selenium (l-seleno methionine), chromium picolinate, zinc glycinate, calcium citrate, and magnesium citrate. For persons over the age of about 51, the composition preferably further comprises one or more of co-enzyme $Q_{10}$, N-acetyl cysteine, and alpha lipoic acid. Preferably, also, vitamin D is added for women over the age of about 36.

5 Claims, No Drawings

(56) References Cited

U.S. PATENT DOCUMENTS

| | | | |
|---|---|---|---|
| 6,660,293 B2 | 12/2003 | Giordano et al. | 424/439 |
| 6,667,063 B2* | 12/2003 | Crum | 424/535 |
| 6,686,340 B2* | 2/2004 | Rath | 514/52 |
| 6,753,325 B2 | 6/2004 | Rosenbloom | 514/167 |
| 6,770,663 B2 | 8/2004 | Wagle et al. | 514/365 |
| 6,797,729 B1 | 9/2004 | Byrne et al. | 514/562 |
| 6,805,880 B1 | 10/2004 | Højgaard et al. | 424/468 |
| 6,814,983 B2 | 11/2004 | Giordano et al. | 424/630 |
| 6,844,012 B1 | 1/2005 | Forceville et al. | 424/702 |
| 6,849,613 B2 | 2/2005 | Prasad et al. | 514/52 |
| 6,863,904 B2 | 3/2005 | Giordano et al. | 424/638 |
| 2002/0146463 A1 | 10/2002 | Clayton | 424/617 |
| 2002/0182196 A1 | 12/2002 | McCleary | 424/94.1 |
| 2002/0182585 A1 | 12/2002 | Kindness et al. | 435/4 |
| 2002/0193323 A1 | 12/2002 | Yegorova | 514/33 |
| 2003/0055012 A1 | 3/2003 | Carter | 514/42 |
| 2003/0103954 A1 | 6/2003 | Rosenbloom | 424/94.1 |
| 2003/0104080 A1 | 6/2003 | Singh et al. | 424/729 |
| 2003/0105027 A1 | 6/2003 | Rosenbloom | 514/18 |
| 2003/0108624 A1 | 6/2003 | Kosbab | 424/729 |
| 2003/0119909 A1 | 6/2003 | Stanislaus | 514/562 |
| 2003/0147981 A1 | 8/2003 | Gillam | 424/770 |
| 2003/0161863 A1 | 8/2003 | Ballevre et al. | 424/439 |
| 2003/0215430 A1 | 11/2003 | Petrus | 424/94.1 |
| 2004/0043013 A1 | 3/2004 | McCleary | 424/94.1 |
| 2004/0082536 A1 | 4/2004 | Cooper et al. | 514/52 |
| 2004/0106674 A1 | 6/2004 | Rich et al. | 514/458 |
| 2004/0109882 A1 | 6/2004 | Schonrock et al. | 424/401 |
| 2004/0223962 A1 | 11/2004 | Riordan | 424/94.63 |
| 2005/0009779 A1 | 1/2005 | Kiliaan et al. | 514/52 |

OTHER PUBLICATIONS

Burkart V, Kioke T, Brenner HH, Imai Y, Kolb H: Dihydrolipoic acid protects pancreatic islet cells from inflammatory attack. Agents Actions 38:60-65, 1993.

Wagh, S.S, et al., "Mode of action of lipoic acid in diabetes", *J. Biosci.*, 11(1-4):59-74 (197).

Niki E. "Mechanisms and Dynamics of Antioxidant Action of Ubiquinol", *Molec. Aspects Med.*, 18:s63-s70 (1997).

Frei, B., "On the Role of Vitamin C and Other Antioxidants in Atherogenesis and Vascular Dysfunction", *Vascular Effects of Antioxidants*, 222(3):196-204 (1999).

Ji, Li Li, "Antioxidants and Oxidative Stress in Exercise", *Antioxidants and Oxidative Stress in Exercise*, 283-292 (1999).

Leeuwenburgh, C., et al. "Oxidative Stress and Antioxidants in Exercise", *Current Medicinal Chemistry*, 8:829-838 (2001).

Holvoet, P. et al. "Oxidized lipoproteins in atherosclerosis and thrombosis", *The FASEB journal*, 8(15):1279-1284 (1994).

Barish, R.J., "In-Flight Radiation: Counseling Patients About Risk", *The Journal of the American Board of Family Practice*, 12(3):195-199 (1999).

Barish, R.J., "Health Physics Concerns in Commercial Aviation", *Health Physics (The Radiation Protection Journal)*, 59(2):199-204 (1990).

Narra, V.R., et al. "Vitamins as Radioprotectors in Vivo, I. Protection by Vitamin C against Internal Radionuclides in Mouse Testes: Implications to the Mechanism of Damage Caused by the Auger Effect", *Radiation Research, An International Journal*, 137(3):394-399 (1994).

Gaziev, A.I., et al., "Effect of vitamin-antioxidant micronutrients on the frequency of spontaneous and in-vitro 3,-ray-induced micronuclei in lymphocytes of donors: the age factor", *Carcinogenesis*, 17(3):493-499 (1996).

Kumar, K.S., et al., "Nutritional Approaches to Radioprotection: Vitamin E", *Military Medicine*, 167(2):57-59 (2002).

Institute of Medicine Report: "Potential Radiation Exposure in Military Operations, Protecting the Soldier Before, During and After", http://www.nap.edu/openbook/0309064392/mtml/55.html, National Academy Press (2000).

DiPaolo, J.A., et al., "In vitro morphologic transformation of Syrian hamster cells by U.V.-irradiation is enhanced by X-irradiation and unaffected by chemical carcinogens", *International Journal Radiat. Biol.*, 30(1):41-53 (1976).

Allard, D.J., CRCPD Liaison to NCRP, (G50) Report on the 2004 Annual Meeting of the NCRP, http://www.crcpd.org/Reports_on_Mtgs/NCRP_Apr04.htm.

"long term consequences of terrorism involving radiation exposure and the release of radioactive materials".

Liptak, G.S., "The Child Who Has Severe Neurologic Impairment", *Physical Assessment*, 45(1):123-144 (1998).

Paterson A., et al., "Helical CT of the Body: Are Settings Adjusted for Pediatric Patients?", *Am. J. Roentgenol*, 176:297-301 (2001).

Patel B., et al.,"Compatibility of calcipotriene with other topical medications", *Journal of the American Academy of Dermatology*, 38:1010-1011 (1998).

Revell, G.M., et al., "Understanding the Child With Special Health Care Needs: A Developmental Perspective", *Journal of Pediatric Nursing*, 6(4):258-268 (1991).

Borek, C., et al., "Selenium and vitamin E inhibit radiogenic and chemically induced transformation in vitro via different mechanisms", *Proc. Natl. Acad. Sci. USA*, 83:1490-1494 (1986).

Stanford W. et al., "Coronary Artery Calcification: Clinical Significance and Current Methods of Detection", *Am. J. Roentgenol*, 161:1139-1146 (1993).

Cascade P.N. et al., "Radiation Exposure to Patients Undergoing Percutaneous Transluminal Cooronary Angioplasty", *Am. J. Cardiol.*, 59:996-997 (1987).

Weiss, J.F., et al., "Radioprotection by Antioxidants", *Annals New York Academy of Sciences*, 899:44-60 (2000).

Sminia P, et al., "Hyperthermia, radiation carcinogenesis and the protective potential of vitamin A and N-acetylcysteine", *J. Cancer Res. Clin. Oncol.*, 122:343-350 (1996).

Ushakova, T. et al., "Modification of Gene Expression by Dietary Antioxidants in Radiation-Induced Apoptosis of Mice Splenocytes", *Free Radical Biology & Medicine*, 26(7-8):887-891 (1999).

Rumberger J.A., et al., "Coronary Heart Disease/Platelet Activation/Myocardial Infarction: Coronary Calcium, as Determined by Electron Beam Computed Tomography, and Coronary. Disease on Arteriogram: Effect of Patient's Sex on Diagnosis" *American Heart Association*, 91(5):1363-1367 (1995).

Ben-Amotz, A., et al., "Effect of natural β-carotene supplementation in children exposed to radiation from the Chernobyl accident", *Radiat. Environ. Biophys.*, 37:187-193 (1998).

Gaziev, A.I., et al., "Dietary supplements of antioxidants reduce hprt mutant frequency in splenocytes of aging mice", *Mutation Research*, 338:77-86 (1995).

Mutlu-Turkoglu, Ü., et al., "The Effect of Selenium and/or Vitamin E Treatments on Radiation —Induced Intestinal Injury in Rats", *Life Sciences*, 66(20):1905-1913 (2000).

Dion, P.W., et al., "The effect of dietary ascorbic acid and α-tocopherol on fecal mutagenicity", *Mutation Research*, 10Z:27-37 (1982).

El-Habit, O.H.M., et al., "The modifying effect of β-carotene on gamma radiation-induced elevation of oxidative reactions and genotoxicity in male rats", *Mutation Research*, 466-179-186 (2000).

Krinsky, N.I., et al., "Antioxidant Functions of Carotenoids", *Free Radical Biology & Medicine*, 7:617-635 (1989).

Ryabchenko, N.I., et al., "Moleculat, Cellular and System. Mechanisms of Radioprotective Action of Polyvitamine Antioxidant Composites" *Radiatsionnaia Biologiia*, 36:895-899 (1996) (In Russian).

Umegaki, K., et al., "Feeding mice palm carotene prevents DNA damage in bone marrow and reduction of peripheral leukocyte counts, and enhances survival following X-ray irradiation", *Carcinogenesis*, 18(10)1943-1947 (1997).

Radner B.S., et al., "Suppression of X-Ray Induced Transformation by Vitamin E in Mouse C3H/10T 1/2 Cells", *Cancer Letters*, 32-25-32 (1986).

Carini, R., et al., "Comparative Evaluation of the Antioxidant Activity of a-Tocopherol, α-Tocopherol α-Polyethylene Glycol 1000 Succinate and α-Tocopherol Succinate in Eolated Hepatocytes and Liver Microsomal Suspensions", *Biochemical Pharmacology*, 39(10) 1597-1601 (1990).

O'Connor, M.K., et al., "A radioprotective effect of vitamin C observed in Chinese hamster ovary cells", *British Journal of radiology*, 50:587-591 (1977).

(56) References Cited

OTHER PUBLICATIONS

Presad, K.N., et al., "Effects of Tocopherol (Vitamin E) Acid Succinate on Morphological Alterations and Growth Inhibition inNIelanoma Cells in Culture", *Cancer Research*, 42:550-555 (1992).
Borek, C., et al., "Ozone acts alone and synergistically with ionizing radiation to induce in vitro neoplastic transformation", *Carcinogenesis*, 7(9)1611-1613 (1986).
Knekt, P., et al., "Body Iron Stores and Risk of Cancer", *Int. J. Cancer*, 56:379-382 (1994).
Holtzman, S., et al., "Synergism of Estrogens and X-Rays in Mammary Carcinogenesis in Female ACI Rats", *J. Natl. Cancer Inst.*, 67(2):455-459 (1981).
Stoker, M. "Effect of X-Irradiation on Susceptibility of Cells to Transformation by Polyoma Virus", *Nature*, 200:756-758 (1963).
Ramakrishnan, N. et al., "Radioprotection of Hematopoietic Tissues in Mice by Lipoic Acid", *Radiation ResearchI*, 130:360-365 (1992).
Killoran, P.L., et al., "Inhibition of Store-Operated Calcium Entry in Human Lymphocytes by Radiation: Protection by Glutathione", *Radiation Research*, 152:611-621 (1999).
Prasad, K.N., et al., "Protective effect off3-mercaptoethylamine and mesenteric vessel clamping on intestine-irradiated rats", *Int. J. Rad. Biol.*, 6(3):257-269 (1962).
Kennedy A.R., et al., "Effects of Retinoids, β-Carotene, and Canthaxanthin on UV- and X-Ray-Induced Transformation of C3H10T1/2 Cells in Vitro", *Nutr. Cancer*, 22:219-232 (1994).
Prasad, K.N., "Modification of the Effect of Tamoxifen cis-Platin DTIC, and Interferon-α2β on Human Melanoma Cells in Culture by a Mixture of Vitamins", *Nutr. Cancer*, 22:233-245 (1994).
Puck, T.T., et al., "Caffeine Enhanced Measurement of Mutagenesis by Low Levels of γ-Irradiation in Human Lymphocytes", *Somatic Cell and Molecular Genetics*, 19(5):423-429 (1993).
Little, J.B., et al., "Influence of Noncarcinogenic Secondary Factors on Radiation Carcinogenesis", *Radiation Research*, 87:240-250 (1981).
Harapanhalli, R.S., et al., "Antioxidant Effects of Vitamin C in Mice Following X-Irradiation", *Research Communications in Molecular Pathology and Pharmacology*, 94(3):271-287 (1996).
Konopacka, M., et al., "Modifying effect of vitamins C, E and beta-carotene against gamma-ray induced DNA damage in mouse cells", *Mutation ResearchI*, 417:85-94 (1998).
Pollack, E.J., etl a. "Radiation Enhancement of SV40 Transformation'In 3T3 and Human Cells", *Nature*, 219:520521 (1968).
Sinclair W.K. "Cysteamine: Differential X-ray Protective Effect on Chinese Hamster Cells During the Cell Cycle", *Science*, 159:442-444 (1968).
*Drug Information for the Healthcare Professional*, Rockville, MD: United States Pharmacopeial Convention, Inc., 2457 (1991).
Hall, E.J., *Radiobiology for the Radiologist*, J.B. Lippincott Co., Philadelphia, PA, (1994).
Wolf, S., "Ch. 6 Radiation Genetics", *Mechanisms in Radiobiology*, Errera M. and Forsberg A., Eds. Academic Press, New York, 441 (1961).
Thomson, J.F., *Radiation Protection in Mammals*, Reinhold, New York, NY (19622.
DiPaolo, J.A., et al., "Kinetics of Syrian Hamster Cells during X-Irradiation Enhancement of Transformation in Vitro by Chemical Carcinogen", *Radiation Research*, 66:310-325 (1976).
*Sources and Effects of Ionizing Radiation*, United Nations Scientific Committee on the Effects of Atomic Radiation UNSCEAR 2000 Report to the General Assembly, with Scientific Annexes, vols. 1 and 2.
Niki, E.; Mechanisms and dynamics of antioxidant action of ubiquinol. Mol Aspects Med. 18 Suppl:S63-70; 1997. (Abstract).
Jacob, S., Henriksen, L, et. al. (1995) Enhancement of glucose disposal in patients with type II diabetes by alpha-lipoic acid. Arzneim Forsch, 45: 872-874. (Abstract).

Suzuki YJ, Tsuchiya M, Packer L: Lipoate prevents glucose-induced protein modifications. Free Rad Res Commun 17:211-217, 1992. (Abstract).
Verlangieri, A. J., Bush, M. J.; Effects of d-alpha-tocorol supplementation on experimentally induced primate atherosclerosis. J Am Coll Nutr. 11:131-138; C 1992. (Abstract).
Hoogwerf, B. J. Young, J. B.; The HOPE study. Ramipril lowered cardiovascular risk, but vitamin E did not. Cleve Clin J Med. 67:287-293; 2000. (Abstract).
Carter, C. A., Pogribny, M.,.Dayidson, A., Jackson, C. D., McGarrity, L. J., Morris, S. M.; Effects of retinoic acid on cell differentiation and reversion toward normal in human endometrial adenocarcinoma (RL95-2) cells. Anticancer Res. 16:17-24; 1996. (Abstract).
Salonen, J. T.; Clinical trials testing cardiovascular benefits of antioxidant supplementation. Free Radic Res. 36:1299-1306; 2002. (Abstract).
Angioplasty and Cardiac Revascularization Treatment and Statistics, American Heart Associate, Heart and Stroke Statistical Update, (2001).
Paranich, A.V., et al., "The role of fat soluble vitamin a and vitamin E in preventing the biological effects of ionizing radiation in rat tissue" *Radiobiologia*, 32:743 (1992).
Prasad, K.N., *Human Radiation Biology*, Harper and Row, New York (1974).
Prasad, K.N., *Handbook of Radiobiology, Second Edition*, CRC Press, Florida (1994).
Radiation Dose Estimates for Radiopharmaceuticals, Radiation Internal Dose Information Center, Oak Ridge Institute for Science and Education (1996).
Og, Ni, et al., "Effect of beta-carotene on 60Co-gamma induced mutation at T-lymphocyte hypoxanthine-guanine phosphoribosyl transferase locus in rats", *Pharmacologic Sinica*, 18:535 (1997).
International Council for Radiation Protection, ICRP publication 33, 1982.
*FDA Centers for Radiologic Health Handbook*: Selected Tissue Doses for Fluoroscopic and Cineangiographic Examination of the Coronary Arteries, 1995.
FDA and Mayo Clinic values of X-ray doses, www.mayohealth.org, Mayo Foundation for Medican Education and Research (2000).
Gopalakristma, R., Gundimeda, U., Chen, Z. Vitamin E Succinate Inhibits Protein Kinase C: Correlation With Its Unique Inhibitory Effects on Cell Growth and Transformation. In: Prasad, K. N., Santamaria L., Williams,R. M., eds. Nutrients in Cancer Prevention and Treatment. Totowa, New Jersey: Humana Press; 1995:21-37.
Frei, B., *Natural Antioxidants in Human Health and Disease*, Academic Press (1994).
Tasinato, A., Boscoboinik, D., Bartoli, G. M. Maroni, P., Azzi, A.; d-alpha-tocopherol inhibition of vascular smooth muscle cell proliferation occurs at physiological concentrations, correlates with protein kinase C inhibition, and is independent of its antioxidant properties. Proc Natl Acad Sci U S A. 92:1210-12194; 1995.
Radi, R., *Nitric oxide, oxidants, and protein tyrosine nitration*, The National Academy of Sciences of the USA (2004).
Tardif, J. C., Cote, G., Lesperance, J., Bourassa, M., Lambert, J., Doucet, S., Bilodeau, L., Nattel, S., de Guise, P.; Probucol and multivitamins in the prevention of restenosis after coronary angioplasty. Multivitamins and Probucol Study Group. N Engl J Med. 337:365-372; 1997.
Brown, B.G. et al., *Simvastatin and Niacin, Antioxidant Vitamins or the Combination for the Prevention of Coronary Disease*, N Engl J Med 345:1583-1592; 2001.
Matthan, N. R. et al., Impact of Simvastatin, niacin, and/or antioxidants on cholesterol metabolism in CAD patients with low HDL, Journal of Lipid Research 44:800-806; 2003.
Gandhi VM, Wagh SS, Natraj CV, Menon KKG: Lipoic acid and diabetes II: mode of action of lipoic acid. J Biosci 9:117-127, 1985.
Earnest, C.P. et al., Complex Multivitamin Supplementation Improves Homocysteine and Resistance to LDL-C Oxidation, Journal of the American College of Nutrition 22:400-407; 2003.
Waters, D. D. Alderman, E. L., Hsia, J., Howard, B. V. Cobb, F. R,. Rogers, W. J., Ouyang, P., Thompson, P. Tardif, J. C. Higgmson, L., Bittner, V., Steffes, M., Gordon, D. J., Proschan, M., Younes, N., Verter, J. L; Effects of hormone replacement therapy and antioxidant vitamin supplements on coronary atherosclerosis in postmenopausal women: a randomized controlled trial. Jama. 288:2432-2440; 2002.

(56) References Cited

OTHER PUBLICATIONS

Schnyder, G., Roffi, M., Flarruner, Y. Pin, R., Hess, O. M.; Effect of homocysteine-lowering therapy with folic acid, vitamin B12, and vitamin B6 on clinical outcome after percutaneous coronary intervention: the Swiss Heart study: a randomized controlled trial. JAMA. 288:973-979; 2002.
Haugaard N, Haugaard ES: Stimulation of glucose utilization by thioctic acid in rat diaphragm incubated in vitro. Biochem Biophys Acta, 222:583-586, 1970.
Singh HPP, Bowman RH: Effect of D, L-alpha lipoic acid on the citrate concentration and phosphofructokinase activity of perfused hearts from normal and diabetic rats. Biochem Biophys Res Commun 41:555-561, 1970.
Brenner DJ, Elliston CD, Hall EJ, Berdon WE: Estimated risks of radiation-induced fatal cancer from pediatric CT, Am J Roentgenol 176: 289-296, 2001.
Witztum, J. L.; The oxidation hypothesis of atherosclerosis. Lancet. 344:793-795; 1994.
Routine vitamin supplementation to prevent cancer and cardiovascular disease: recommendations and rationale. Ann Intern Med. 139:51-55; 2003.
Prasad KN, Cole WC, and Haase GM: Health risk of low dose ionizing radiation in humans: A review. Exp. Biol Med 229:378-382, 2004.
Riley, S. J., Stouffer G. A.; Cardiology Grand Rounds from the University of North Carolina at Chapel Hill. The antioxidant vitamins and coronary heart disease: Part 1. Basic science background and clinical observational studies. Am J Med Sci. 324:314-320; 2002.
Riley, S. J., Stouffer, G. A.; Cardiology Grand Rounds from the University of North Carolina at Chapel Hill. The antioxidant vitamins and coronary heart disease: Part II. Randomized clinical trials. Am J Med Sci. 325:15-19; 2003.
Morris, C. D., Carson S.; Routine vitamin supplementation to prevent cardiovascular disease: a summary of the evidence for the U.S. Preventive Services Task Force. Ann Intern Med. 139:56-70; 2003.
Reaven, P. D., Khouw, A., Beltz, W. F., Parthasarathy,S. Witztum J. L.; Effect of dietary antioxidant combinations in humans. Protection of Ldl by vitamin E but not by beta-carotene. Arterioscler Thromb. 13:590-600; 1993.
de Nigras, F. Youssef, T., Ciafre, S., Franeoni, F., Anania, V., Condorelli, G., Palinski, W., Napoli, C.; Evidence r oxidative activation of c-Myc-dependent nuclear signaling in human coronary smooth muscle cells and in early lesion of Watanabe heritable hyperlipidemic rabbits: protective effects of vitamin E. Circulation. 102:2111-2117; 2000.
Mann, M. J. Whittemore, A. D., Donaldson, M. C. Belkin, M., Conte, M. S., Polak, J. F., Orav, E. J., Ehsan, A., Dell'Acgua, G., Dzau, V. J.• Ex-vivo gene therapy of human vascular bypass grafts with E2F decoy. the PREVENT single-centre, randomised, controlled trial. Lancet. 354:1493-1498; 1999.
Becker, A. E., de Boer, O. J., van Der Wal, A. C.; The role of inflammation and infection in coronary artery disease. Annu Rev Med. 52:289-297; 2001.
Napoli, C., Ignarro, L. J.; Nitric oxide and atherosclerosis. Nitric Oxide. 5:88-97; 2001.
Ignarro, L. J., Cirino, G., Casini, A., Napoli, C.; Nitric oxide as a signaling molecule in the vascular system: an overview. J Cardiovasc Pharmacol. 34:879-886; 1999.
Anderson, T. J. Gerhard, M. D., Meredith, I. T., Charbonneau, F., Delagrange, D., Creager, M. A., Selwyn, A. P. Ganz, P. Systemic nature of endothelial dysfunction in atherosclerosis. Am J Cardiol. 75:71B-74B; 1995.
Drexler, H.; Nitric oxide and coronary endothelial dysfunction in humans. Cardiovasc Res. 43:572-579; 1999.
Luoma, J. S., Yla-Herttuala, S.; Expression of inducible nitric oxide synthase in macrophages and smooth muscle cells in various types of human atherosclerotic lesions. Virchows Arch. 434:561-568; 1999.

Gum, P. A., Kottke-Marchant, K., Welsh, P. A., White, J., Topol, E. J.; A prospective, blinded determination of the natural history of aspirin resistance among stable patients with cardiovascular disease. J Am Coll Cardiol. 41:961-965; 2003.
Cotter, G., Shemesh, E., Zehavi, M., Dinur,.I., Rudnick, A., Milo, O., Vered, Z., Krakover, R., Kaluslci, E. Kornberg, A.; Lack of aspirin effect: aspirin resistance or resistance to taking aspirin? Am Heart J. 147:293-300; 2004.
Gum, P. A. Kottke-Marchant, K., Poggio, E. D., Gurm, H., Welsh, P. A., Brooks, L., Sapp, K., Topol, E. J.; Profile and prevalence of as resistance in patients with cardiovascular disease. Am J. Cardiol. 88:230-235; 2001.
Lynch, S., Frei, B. Antioxidants as Antiatherogens: Animal Studies. In: Frei, B., ed. Natural Antioxidants in Human Health and Disease. New York: Academic Press; 1994:353-385.
Smith, T. L., Kununerow, F. A.; Effect of dietary vitamin E on plasma lipids and artherogenesis in restricted ovulator chickens. Atherosclerosis. 75:105-109; 1989.
Woicicki, J., Rozewicka, L., Barcew-Wiszniewska, B., Samochowiec, L., Juzwiak, S., Kadlubowska, D., Tustanowski, S., Juzyszyn, Z.; Effect of selenium and vitamin E on the development of experimental atherosclerosis in rabbits. Atherosclerosis. 87:9-16; 1991.
Calzada, C. Bruckdorfer, K. R., Rice-Evans, C. A.; The influence of antioxidant nutrients on platelet function in healthy volunteers. Atherosclerosis. 128:97-105; 1997.
Colette, C. Pares-Herbute, N., Monnier, L. H., Cartry, E.; Platelet function in type I diabetes: effects of supplementation with large doses of vitamin E. Am J Clin Nutr. 47:256-261; 1988.
de Lorgeril, M., Boissonnat, P., Salen, P., Mon and I. Monnez, C., Guidollet, J., Ferrera, R., Dureau, G., Ninet, J., Renaud, S.;. The beneficial effect of dietary, antioxidant supplementation on platelet aggregation and cyclosporine treatment in heart transplant recipients. Transplantation. 58:193-195; 1994.
Adams, M. R., Kinlay, S., Blake, G. J., Orford, J. L., Ganz, P., Selwyn, A. P.; Atherogenic lipids and endothelial dysfunction: mechanisms in the genesis of ischemic syndromes. Annu Rev Med. 51:149-167; 2000.
Cohrs, R. J., Torelli, S. Prasad, K. N., Edwards-Prasad, J., Sharma, O. K.; Effect of vitamin E succinate and a cAMP-stimulating agent on the expression of c-myc and N-myc and H-ras in murine neuroblastoma cells. Int J Dev Neurosci. 9:187-194; 1991.
Gey, K. F. Puska, P.; Plasma vitamins E and a inversely correlated to mortality from ischemic heart disease in cross-cultural epidemiology. Ann N Y Acad Sci. 570:268-282;.
Riemersma, R. A., Wood, D. A., Macintyre, C. C., Elton, R. A., Gey, K. F., Oliver, M. F.; Risk of angina pectoris and plasma concentrations of vitamins A, C, and E and carotene. Lancet. 337:1-5; 1991.
Rimm, E. B. Stampfer, M. J., Ascherio, A., Giovannucci, E., Colditz, G. A. Willett, W. C.; Vitamin E consumption and the risk of coronary heart disease in men. N Engl J Med. 328:1450-1456; 1993. (Abstract).
Stampfer, M. J., Hennekens, C. H., Manson, J. E., Colditz, G. A., Rosner, B., Willett, W. C.; Vitamin E consumption and the risk of coronary disease in women. N Engl J Med. 328:1444-1449; 1993. (Abstract).
Losonczy, K. G., Harris, T. B. Havlik, R. J.; Vitamin E and vitamin C supplement use and risk of all-cause and coronary. heart disease mortality in older persons: the Established Populations for Epidemiologic Studies of the Elderly. Am J Clin Nutr. 64:190-196; 1996.
Salonen, J. T., Salonen, R., Penttila, I., Herranen, J. Jauhiainen, M., Kantola, M., Lappetelainen, R., Maenpaa, P. H., Alfthan, G. Puska, P.; Serum fatty acids, apofipoproteins, selenium and vitamin antioxidants and the risk of death from coronary artery disease. Am J Cardiol. 56:226-231; 1985.
Kok, F. J. de Bruin, A. M. Vermeeren, R., Hofman, A., van Laar,. A., de Bruin, M., Hermus, R. J., Valkenburg, H. A.; Serum selenium, vitamin antioxidants, and cardiovascular mortality: a 9-year follow-up study in the Netherlands. Am J Clin Nutr. 45:462-468; 1987.

(56) References Cited

OTHER PUBLICATIONS

Heitzer, T., Yla Herttuala, S., Wild, E., Luoma, J., Drexler, H.; Effect of vitamin E on endothelial vasodilator function in patients with hypercholesterolemia, chronic smoking or both. J Am Coll Cardiol. 33:499-505; 1999.

Wilkinson, I. B., Megson, I. L., MacCallum, T., Rooijmans, D. F., Johnson, S. M., Boyd, J. L. Cockcroft, J. R., Webb, D. J.; Acute methionine loading does not alter arterial stiffness L., J Cardiovasc Pharmacol. 37:1-5; 2001. In.

Stephens, N. G., Parsons, A., Schofield, P. M., Kelly, F., Cheeseman, K., Mitchinson,. M. J.; Randomised controlled trial of vitamin E in patients with coronary disease: Cambridge Heart Antioxidant Study (CHAOS). Lancet. 347:781-786; 1996.

Jialal, I., Devaraj, S.; Vitamin E supplementation and cardiovascular events in high-risk patients. N Engl J Med. 342:1917-1918; 2000.

Weinberg, R. B., VanderWerken, B. S., Anderson, R. A., Stegner, J. E., Thomas, M. J.; Pro-oxithnt effect of vitamin E in cigarette smokers consuming a high polyunsaturated fat diet. Arterioscler Thromb Vasc Biol. 21:1029-1033; 2001.

DeMaio, S. J. King, S. B. 3rd, Lembo, .N. J., Roubin, G. S., Hearn, J. A., Bhagavan, H. N., Sgoutas, D. S.; Vitamin B., plasma lipids and incidence of restenosis after percutaneous transluminal coronary angioplasty (PTCA). J Am Coll Nutr. 11:68-73; 1992.

Devaraj, S., Jialal, I.; Alpha tocopherol supplementation decreases serum C-reactive protein and monocyte interleukin-6 levers in normal volunteers and type 2 diabetic patients. Free Radic Biol Med. 29:790-792; 2000.

Islam, K. N. O'Byrne, D., Devaraj, S., Palmer, B., Grundy, S. M., Jialal, I:, Alpha-tocopherol supplementation decreases the oxidative susceptibility of LDL in renal failure patients on dialysis therapy. Atherosclerosis. 150:217-224; 2000.

Rapola, J. M., Virtamo, J., Ripatti, S., Huttunen, J. K. Albanes, D., Taylor, P. R., Hemonen, O. P.; Randomised-trial of alpha-tocopherol and beta-carotene supplements on incidence of major coronary events in men with previous myocardial infarction. Lancet. 349:1715-1720; 1997.

Fang, J. C., Kinlay, S., Beltrame, J., Hikiti, H. Wainstein, M. Behrendt, D., Suh, J., Frei, B., Mudge, G. H., Selwyn, A. P., Ganz, P.; Effect of vitamins ,C and E on progression of transplant-associated artenosclerosis: a randomised trial. Lancet. 359:1108-1113; 2002.

Upritchard, J. E., Sutherland, W. H., Mann, J. I.; Effect of supplementation with tomato juice, vitamin E, and vitamin C on LDL oxidation and products of inflammatory activity in type 2 diabetes. Diabetes Care. 23:733-738; 2000.

Beckman, J. A., Goldfine, A. B., Gordon, M. B., Creager, M. A.; Ascorbate restores endothelium-dependent vasodilation impaired by acute hyperglycemia in humans. Circulation. 103:1618-1623; 2001.

Plotnick, G. D., Corretti, M. C., Vogel, R. A.; Effect of antioxidant vitamins on the transient impairment of endothelium-dependent brachial artery vasoactivity following a single high-fat meal. Jama. 278:1682-1686; 1997.

Redlich, C. A. Chung, J. S., Cullen, M. R., Blaner, W. S., Van Bennekum, A. M., Berglund, L.; Effect of long-term beta-carotene and vitamin a. On serum cholesterol and trigrycende leyels among participants in the Carotene and Retinol Efficacy Trial (CARET). Atherosclerosis. 143:427-434; 1999.

Neunteufl, T., Kostner, K., Katzenschlager, R., Zehetgruber, M., Maurer, G., Weidinger, F.; Additional benefit of vitamin E supplementation to simvastatin therapy on vasoreactivity of the brachial artery of hypercholesterolemic men. J Am Coll Cardiol. 32:711-716; 1998.

Langsjoen, P. H. Folkers, K.; Long-term efficacy and safety of coenzyme Q10 therapy for idiopathic dilated cardiomyopathy. Am J Cardiol. 65:521-523; 1990.

Hodis, H. N. Mack, W. J., LaBree, L., Cashin-Hemphill, L., Sevanian, A., Johnson, R., Azen, S. P.; Serial coronary angiographic evidence that antioxidant vitamin intake reduces progression of coronary artery atherosclerosis. Jama. 273:1849-1854; 1995.

Collins, R., Peto, R., Armitage, J.; The MRC/BHF Heart Protection Study: preliminary results. Int J Clin Pract. 56:53-56; 2002.

Cheung, M. C., Zhao, X. Q., Chait, A. Albers, J. J., Brown, B. G.; Antioxidant supplements block the response of HDL to simvastatin-niacin therapy in patients with coronary artery disease and low HDL. Arterioscler Thromb Vasc Biol. 21:1320-1326; 2001.

Zhang, L. X., Cooney, R. V., Bertram, J. S.; Carotenoids up-regulate connexin43 gene expression independent of their provitamin a or antioxidant properties. Cancer Res. 52:5707-5712; 1992.

Hazuka, M. B., Edwards-Prasad, J., Newman, F., Kinzie, J. J., Prasad, K. N.; Beta-carotene induces morphological differentiation and decreases adenylate cyclase activity in melanoma cells in culture. J Am Coll Nutr. 9:143-149; 1990.

Jessup, W.; Oxidized lipoproteins and nitric oxide. Curr Opin Lipidol. 7:274-280; 1996. (Abstract).

Vile, G. F., Winterbourn, C. C.; Inhibition of adriamycin-promoted microsomal lipid peroxidation by beta-carotene, alpha-tocopherol and retinol at high and low oxygen partial pressures. FEBS Lett. 238:353-356; 1988.

Niki, E.; Interaction of ascorbate and alpha-tocopherol. Ann N Y Acad Sci. 498:186-199; 1987.

Prasad, K. N., Kumar, B. Yan, X. D., Hanson, A. J., Cole, W. C.; Alpha-tocopheryl succinate, the most effective form of vitamin for adjuvant cancer treatment: a review. J Am Coll Nutr. 22:108-117; 2003.

Ingold, K. U., Burton, G. W., Foster, D. O., Hughes, L., Lindsay,D. A., Webb, A.; Biokinetics of and discrimination between dietary RRR- and SRR-alpha-tocopherols in the male rat. Lipids. 22:163-172; 1987.

Witschi, A. Reddy, S. Stofer, B. Lauterburg B. H.; The systemic availability of oral glutathione. Eur J Clin Phannacol. 43:667-669; 1992.

Stoyanovsky, D. A., Osipov, A. N., Quinn, P. J. Kagan, V. E.; Ubiquinone-dependent recycling of vitamin E radicals by superoxide. Arch Biochem Biophys. 323:343-351; 1995.

Abate, A., Yang, G., Dennery, P. A., Oberle, S., Schroder, H.: Synergistic inhibition of cyclooxygenase-2 expression by vitamin E and aspirin. Free Radic Biol Med. 29:1135-1142; 2000.

Alessio H. (1993). Exercise-induced oxidative stress. Medicine & Science in Sports & Exercise, 25:218-22.

Clarkson PM, Nosaka K, & Braun B. (1992). Muscle function after exercise-induced muscle damage and rapid adaptation. Medicine & Science in Sports & Exercise, 24:512-520.

Halliwell B, Gutteridge JM & Cross CE. (1992). Free radicals, antioxidants and human disease: where are we now? Journal Laboratory Clinical Medicine, 119:598-620.

Jenkins PR & Goldfarb A (1993). Introduction: oxidant stress, aging, and exercise. Medicine & Science in Sports & Exercise, 25:210-212.

Nagamatsu, M., Nickander, K.K. Schmelzer, J.D. et al. (1995). Lipoic acid improves nerve blood flow, reduces oxidative stress, and improves distal nerve conduction in experimental diabetic neuropathy. Diabetes Care,18: 1160-1167.

Meydani M, Evans WJ, Handelman G, biddle L, Fielding RA, Meydani SN, Burrill J, Fiatarone MA, Blumberg IB & Cannonn JG (1994). Protective effect of vitamin E on -induced oxidative damage in young and old adults. American Journal of Physiology, 264:R992.

Prasad, K.N., Cole W. and Hovland P. (1998) Cancer prevention studies: past, present and future direactions. Nutrition ,14: 197-210.

Natraj CV, Gandhi VM, Menon KKG: Lipoic acid and Diabetes I: effect of dihydrolipoic acid administration in diabetic rats and rabbits. J. Biosci 6:37-46, 1984.

Wagh SS, Gandi VM, Natraj CV, Menon KKG: Lipoic acid and diabetes-III: metabolic role of acetyl dihydrolipoic acid. J Biosci 10:171-179, 1986.

Faust A, Burkart V, Ulrich H, Weischer CH, Kolb H: Effect of lipoic acid on cyclophosphamide-induced diabetes and insulinitis in non-obese diabetic mice. Int. J. Inununophармacol 16:61-66, 1994.

* cited by examiner

MULTIPLE ANTIOXIDANT MICRONUTRIENTS

CROSS REFERENCE TO RELATED APPLICATIONS

We claim the benefit under Title 35, United States Code §120 of U.S. application Ser. No. 10/229,271 filed Aug. 28, 2002, which has been allowed, and which, in turn, claims the benefit of the priority of Provisional Application No. 60/315,523 filed Aug. 29, 2001, entitled MULTIPLE ANTIOXIDANT MICRONUTRIENTS FOR OPTIMAL HEALTH.

BACKGROUND OF THE INVENTION

In the beginning, the earth's atmosphere had no oxygen. Anaerobic organisms, which can live without oxygen, were thriving. About 2.5 billion years ago, blue-green algae in the ocean acquired the ability to split water into hydrogen and oxygen and this chemical reaction initiated the release of oxygen into the atmosphere. The increased levels of atmospheric oxygen caused extinction of many anaerobic organisms owing to oxygen's toxicity. This important biological event also led to the evolution of multicellular organisms, including humans, who utilize oxygen for survival. The content of oxygen in the air gradually increased to the current amounts of about 21 percent in dry air and about 34 percent in water. The use of oxygen by any organism generates free radicals that are toxic. Therefore, during this period of atmospheric oxygenation, organisms must have struggled to survive the sudden exposure to oxygen toxicity. There must have been enormous rearranging of nucleotides in genes to produce specific proteins that could protect organisms against the damage produced by free radicals.

This process eventually led to the production of three antioxidant enzymes. Superoxide dismutase (SOD) requires manganese, copper, or zinc for its biological activity. Mn-SOD is present in mitochondria, whereas Cu-SOD and Zn-SOD are present in the cytoplasm and nucleus of the cell. All three can destroy free radicals and hydrogen peroxide. Another enzyme, catalase, requires iron for its biological activity and it destroys $H_2O_2$ in cells. Human tissue also contains glutathione peroxidase which requires selenium for its biological activity. It is also responsible for removing hydrogen peroxide.

Although iron, copper, and manganese are essential for the activities of antioxidant enzymes, a slight excess of free iron, Cu, or Mn can increase the production of free radicals, and subsequently enhance the risk of various chronic diseases. In addition, organisms, including mammals, consume certain antioxidants that are needed for growth and survival from plant sources. These antioxidants include carotenoids, vitamins A, C, and E, flavonoids, polyphenols, and herbal antioxidants.

Currently, the doses of antioxidants for the greatest benefit to human health are not well established. Nevertheless, increasing numbers of people are taking some form of supplements in the hope that it will optimize their health. Unfortunately, at present, they rely on advice from health-related magazines, books, advertising, radio and television reports or vitamin store salespeople. In fact, most people consume these nutrients without any scientific rationale. Furthermore, the majority of vitamin/mineral preparations have not given adequate attention to the dose, type, and chemical form of antioxidants, and appropriate minerals and other micronutrients.

SUMMARY OF THE INVENTION

The present invention is directed to a method for optimizing the health of humans according to their age and sex comprising administering to said humans a daily dose of a multiple antioxidant micronutrient composition comprising vitamin A (palmitate), beta-carotene (from natural d. salina), vitamin C (calcium ascorbate), vitamin D-3 (cholecalciferol), natural source vitamin E including both d-alpha tocopherol and d-alpha tocopheryl acid succinate, thiamine mononitrate, riboflavin, niacinamide ascorbate, d-calcium pantothenate, pyridoxine hydrochloride, cyanocobalamin, folic acid (folacin), d-biotin, selenium (l-seleno methionine), chromium picolinate, zinc glycinate, calcium citrate, and magnesium citrate.

For persons over the age of about 51, the composition preferably further comprises one or more of co-enzyme $Q_{10}$, N-acetyl cysteine, and alpha lipoic acid. Preferably, also, vitamin D is added for women over the age of about 36.

DETAILED DESCRIPTION OF THE INVENTION

Generally healthy patients on an optimal preventive health formula are routinely categorized by age and sex, i.e.,
  Ages 13 to 17 years, male and female;
  Ages 18 to 35 years, male and female;
  Ages 36 to 50 years, male;
  Ages 36 to 50 years, female;
  Ages 51 to 65 years, male;
  Ages 51 to 65 years, female;
  Ages 66 and over, male; and
  Ages 66 and over, female.

Most commercially available multiple supplement formulations contain iron, copper, and/or manganese. It is well known that these substances actively generate free radicals when combined with vitamin C. In addition, these minerals are more easily absorbed from the intestinal tract in the presence of antioxidants, such as vitamin C, and thereby increase the body stores of these minerals. Increased iron stores have been associated with many chronic human conditions, including heart disease, cancer, and neurological diseases. Therefore, the addition of iron, copper, or manganese to any multiple antioxidant preparation has no scientific merit for optimal health or disease prevention. Only in cases where a person has iron-deficiency anemia, is a short-term iron supplement essential.

Many commercially available preparations contain heavy metals such as boron, vanadium, and molybdenum. Sufficient amounts of these metals are obtained from the diet and the daily consumption of excess amounts over a long period of time can be neurotoxic.

Many commercial preparations contain inositol, methionine, and choline in varying amounts, e.g., 30 mg to 60 mg. These small doses serve no useful purpose for improving health because 400 mg to 1000 mg of these nutrients are obtained daily from even the most minimal diet.

Para-aminobenzoic acid (PABA) is present in some multiple vitamin preparations. PABA has no biologic function in mammalian cells and can block the antibacterial effect of sulfonamides. Therefore, the effectiveness of a sulfonamide may be reduced in some patients being treated for a bacterial infection.

Commercially sold multiple antioxidant preparations often contain varying amounts of N-acetyl cysteine or alpha lipoic acid. These nutrients are utilized because they are known to increase glutathione levels in the cells. Reduced glutathione is a powerful antioxidant and actively protects both normal and cancer cells against radiation damage. Many cancer patients take antioxidant supplements without the knowledge of their oncologists. Therefore, the consumption of antioxidant preparations containing N-acetyl cysteine or alpha lipoic acid by these patients undergoing radiation therapy could interfere with important anti-cancer treatment.

The addition of both beta-carotene and vitamin A to any multiple vitamin preparation is essential, because beta-carotene not only acts as a precursor of vitamin A, but also performs important biological functions that cannot be performed by vitamin A. Beta-carotene increases the expression of the connexin gene, which codes for a gap junction protein that is necessary for maintaining the normal cellular phenotype. While other carotenoids, such as lycopene, xanthophylls, and lutein, are also important for health, they can be obtained from an adequate diet with tomato (lycopene), spinach (lutein), and paprika (xanthophylls) in amounts that are higher than those that can be supplied from supplements. Therefore, the addition of a few milligrams of lycopene, xanthophylls, and lutein to any multiple vitamin preparation serves no useful purpose for health or disease prevention.

The proper ratio of two forms of vitamin E, d-alpha tocopherol, which is normally present in the body, and d-alpha tocopheryl succinate, to a multiple antioxidant preparation is essential. Alpha tocopheryl succinate is the most effective form of vitamin E inside the cells, whereas alpha tocopherol can readily act as an antioxidant in the intestinal tract and in the extracellular enviroment of the body. Alpha-tocopherol at doses of 20-60 µg/ml can stimulate the immune system, while the beta, gamma, and delta forms at similar doses can inhibit immune system. This effect of these forms of tocopherol may not be related to their antioxidant action and, since they are less effective than alpha tocopherol, their supplementation is not recommended.

Tocotrienols are also antioxidants, but they may inhibit cholesterol synthesis. Since this activity is not beneficial in healthy individuals, prolonged consumption of tocotrienols as a supplement is not optimal.

Vitamin C is usually administered as ascorbic acid, which can cause stomach upset, diarrhea, and other complications in some individuals. However, using the calcium ascorbate form is most suitable because it is non-acidic and has not been shown to produce negative side effects. The use of potassium ascorbate and magnesium ascorbate in any multiple vitamin preparation is unnecessary. Also, any multiple micronutrient preparation should include adequate amounts of B-vitamins (2-3 times of RDA) and appropriate minerals.

A supplement that attempts to include all antioxidants or micronutrients without regard to age, sex, general health and disease status, is irrational and cannot be recommended. It appears more appropriate to utilize a basic antioxidant formulation that contains the necessary nutrients for optimal health, and then supplement that product with additional nutrients based on the above individual factors.

A balanced diet may be sufficient for normal growth, but supplemental micronutrients, including antioxidants, are important for optimal health. With the current typical American diet, one would have difficulty eating fresh fruit and vegetables daily in the amounts and at the frequencies each day necessary to maintain sustained optimal levels of beta-carotene and vitamins A, C, and E in body tissues. In addition, when one travels away from home, the availability of these vital foods may be limited. While some scientists believe that a balanced diet is sufficient for maintaining optimal health, many studies suggest that most foods contain naturally occurring toxic, as well as protective, substances. While a balanced diet may prevent vitamin deficiency, it may not be sufficient for disease prevention since the concept of "balance" may vary markedly from one individual to another. In addition, environmental sources of toxins (such as pesticides) may well vary from region to region.

Another advantage of the supplements of the present invention is that they can be consumed at the most appropriate time to maximize their effectiveness in preventing the formation of toxic chemicals (mutagens and carcinogens) in the gastrointestinal tract during digestion. For example, if vitamins C and E are taken immediately before eating nitrite-rich food, the formation of mutagenic nitrosamines in the stomach may be reduced, whereas taking these vitamins a few hours after such a meal may not be effective in reducing the formation of this cancer-causing substance. Furthermore, studies have demonstrated that levels of fecal mutagens (a possible source of cancer) in people who regularly eat meat are much higher than in vegetarians. Ingestion of vitamins C and E has been shown to reduce the levels of mutagens in the feces. Therefore, these supplements should be taken before, or right after, eating meat, whereas consuming them several hours after such a meal may not be as effective.

The risk of chronic illnesses may depend upon the relative consumption of protective versus toxic substances. If the daily intake of protective substances is higher than toxic agents, the incidence of chronic illness may be reduced. Since we know very little about the relative levels of toxic and protective substances in any diet, a daily supplement of micronutrients including antioxidants would assure a higher level of preventive protection.

Free radicals are examples of primary agents involved in increasing the risk of cancer, heart disease, and neurological disease. If they damage normal dividing cells, the risk of cancer is increased. If they damage non-dividing cells, such as neurons, the risk of neurological diseases is enhanced. Therefore, quenching free radicals with antioxidants is important for the maintenance of optimal health.

The basic micronutrient formulation of the present invention satisfies all of the required components previously outlined and provides a foundation for a maximally effective preventive formula for otherwise healthy people. Since the biological half-life of most micronutrients is much less than 12 hours, it is essential to take these supplements twice a day.

In older age groups (greater than 50 years), the addition of co-enzyme $Q_{10}$ is important because it may improve mitochondrial function and increase energy level. In addition, the likelihood of mitochondrial damage increases with age.

Furthermore, the sulfhydryl compounds, such as glutathione, are important antioxidants that protect cells against free radical damage. Although glutathione levels decrease with aging, it cannot be taken as a supplement because it is completely destroyed during digestion. Therefore, N-acetyl cysteine and alpha lipoic acid, which increase cellular levels of glutathione, are recommended for older individuals.

To reduce the risk of osteoporosis in women, an appropriate calcium/magnesium preparation with vitamin D is required. The citrate form is most efficiently absorbed where as the oxide form is not. The presence of vitamin D increases the absorption of calcium from the intestinal tract. This supplementation is especially important after menopause where the loss of calcium increases with age.

SUGGESTED DAILY FORMULATION

Ages 13-17 years, male and female:

| | |
|---|---|
| vitamin A (palmitate) | 2,500 I.U. |
| beta-carotene (from natural d. salina) | 7.5 mg |
| vitamin C (calcium ascorbate) | 250 mg |
| vitamin D-3 (cholecalciferol) | 200 I.U. |
| natural source vitamin E | |
| (d-alpha tocopherol) | 50 I.U. |
| (d-alpha tocopheryl acid succinate) | 50 I.U. |
| thiamine mononitrate | 2 mg |
| riboflavin | 2.5 mg |
| niacinamide ascorbate | 15 mg |
| d-calcium pantothenate | 5 mg |
| pyridoxine hydrochloride | 2.5 mg |
| cyanocobalamin | 5 μg |
| folic acid (folacin) | 400 μg |
| d-biotin | 100 μg |
| selenium (l-seleno methionine) | 50 μg |
| chromium picolinate | 25 μg |
| zinc glycinate | 7.5 mg |
| calcium citrate | 125 mg |
| magnesium citrate | 62.5 mg |

Ages 18-35 years, male:

| | |
|---|---|
| vitamin A (palmitate) | 5,000 I.U. |
| beta-carotene (from natural d. salina) | 15 mg |
| vitamin C (calcium ascorbate) | 500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 100 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |

Ages 36-50 years, male:

| | |
|---|---|
| vitamin A (palmitate) | 5,000 I.U. |
| beta-carotene (from natural d. salina) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 mcg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |

For women, the following supplements should be added:

| | |
|---|---|
| calcium citrate | 1,500 mg |
| magnesium citrate | 750 mg |
| vitamin D | 100 I.U. |

Ages 51-65 years, male:

| | |
|---|---|
| vitamin A (palmitate) | 5,000 I.U. |
| beta-carotene (from natural d. salina) | 15 mg |
| vitamin C (calcium ascorbate) | 1,500 mg |
| vitamin D-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |
| co-enzyme $Q_{10}$ | 30 mg |
| n-acetyl cysteine | 250 mg |

For women, the following supplements should be added:

| | |
|---|---|
| calcium citrate | 1,500 mg |
| magnesium citrate | 750 mg |
| vitamin D | 100 I.U. |

Age 66 and over, male:

| | |
|---|---|
| vitamin A (palmitate) | 5,000 I.U. |
| beta-carotene (from natural d. salina) | 15 mg |
| vitamin C (calcium ascorbate) | 2,500 mg |
| vitamin d-3 (cholecalciferol) | 400 I.U. |
| natural source vitamin E | |
| (d-alpha tocopherol) | 100 I.U. |
| (d-alpha tocopheryl acid succinate) | 300 I.U. |
| thiamine mononitrate | 4 mg |
| riboflavin | 5 mg |
| niacinamide ascorbate | 30 mg |
| d-calcium pantothenate | 10 mg |
| pyridoxine hydrochloride | 5 mg |
| cyanocobalamin | 10 μg |
| folic acid (folacin) | 800 μg |
| d-biotin | 200 μg |
| selenium (l-seleno methionine) | 100 μg |
| chromium picolinate | 50 μg |
| zinc glycinate | 15 mg |
| calcium citrate | 250 mg |
| magnesium citrate | 125 mg |
| co-enzyme $Q_{10}$ | 30 mg |
| n-acetyl cysteine | 250 mg |
| alpha lipoic acid | 30 mg |

For women, the following supplements should be added:

| | |
|---|---|
| calcium citrate | 1,500 mg |
| magnesium citrate | 750 mg |
| vitamin D | 100 I.U. |

It will be understood that, in addition to antioxidant micronutrients, diet and lifestyle recommendations from the healthcare professional are also very important in maintaining optimal health and preventing disease risk. For example, in the diet, one should increase consumption of fresh fruits and vegetables; increase consumption of fiber (26 grams per day) from fruits, vegetables, and fiber-rich cereals; reduce fat consumption to 20 percent of total calories (1 gram of fat equals nine calories); avoid excessive calories; reduce consumption of food with high nitrate or nitrite content (e.g. preserved meats) and whenever eating such foods, first consume antioxidants; avoid excessive amounts of charcoal-broiled or smoked meat or fish; reduce the consumption of pickled fruits and vegetables; reduce the consumption of caffeine containing beverages; and, for women age 36 and older, consume a calcium-rich diet.

Additionally, one should:
1. avoid drinking excessive amounts of alcohol;
2. NOT SMOKE or chew tobacco and should avoid exposure to second-hand smoke;
3. exercise 3 to 5 days a week for 30 minutes and, if doing aerobic exercise for 30 minutes or more, take antioxidant supplements beforehand;
4. adopt a lifestyle of reduced stress; and
5. avoid excessive sun exposure and use of UV light for skin tanning or hyperbaric oxygen "cocktails" for energy bursts.

What is claimed is:

1. A composition for administration to male and female humans consisting of:
   vitamin A
   beta-carotene
   vitamin C
   vitamin D-3
   vitamin E
   thiamine mononitrate
   riboflavin
   niacinamide ascorbate
   d-calcium pantothenate
   pyridoxine hydrochloride
   cyancobalamin
   folic acid
   d-biotin
   selenium
   chromium picolinate
   zinc glycinate
   calcium citrate
   magnesium citrate
   co-enzyme Q10, n-acetyl cysteine, alpha lipoic acid and vitamin D.

2. A composition for administration to male and female humans consisting of:
   vitamin A
   beta-carotene
   vitamin C
   vitamin D-3
   vitamin E
   thiamine mononitrate
   riboflavin
   niacinamide ascorbate
   d-calcium pantothenate
   pyridoxine hydrochloride
   cyancobalamin
   folic acid
   d-biotin
   selenium
   chromium picolinate
   zinc glycinate
   calcium citrate
   magnesium citrate, and
   Vitamin D.

3. A composition for administration to male and female humans consisting of:
   vitamin A
   beta-carotene
   vitamin C
   vitamin D-3
   vitamin E
   thiamine mononitrate
   riboflavin
   niacinamide ascorbate
   d-calcium pantothenate
   pyridoxine hydrochloride
   cyancobalamin
   folic acid
   d-biotin
   selenium
   chromium picolinate
   zinc glycinate
   calcium citrate
   magnesium citrate
   co-enzyme Q10, and
   n-acetyl cysteine.

4. A composition for administration to male and female humans consisting of:
   vitamin A
   beta-carotene
   vitamin C
   vitamin D-3
   vitamin E
   thiamine mononitrate
   riboflavin
   niacinamide ascorbate
   d-calcium pantothenate
   pyridoxine hydrochloride
   cyancobalamin
   folic acid
   d-biotin
   selenium
   chromium picolinate
   zinc glycinate
   calcium citrate
   magnesium citrate
   co-enzyme Q10
   n-acetyl cysteine and
   Vitamin D.

5. A composition for administration to male and female humans consisting of:
   vitamin A
   beta-carotene
   vitamin C
   vitamin D-3
   vitamin E
   thiamine mononitrate
   riboflavin
   niacinamide ascorbate d-calcium pantothenate
pyridoxine hydrochloride
cyancobalamin
folic acid
d-biotin
selenium
chromium picolinate
zinc glycinate
calcium citrate
magnesium citrate
co-enzyme Q10
n-acetyl cysteine, and
alpha lipoic acid.

* * * * *